United States Patent [19]
Leistner et al.

[11] Patent Number: 5,985,671
[45] Date of Patent: Nov. 16, 1999

[54] MEASURING SYSTEM AND METHOD FOR PERFORMING LUMINOMETRIC SERIES ANALYSES AS WELL AS MULTIPLE CUVETTE FOR RECEIVING LIQUID SAMPLES THEREFOR

[75] Inventors: Hermann Leistner, Birkenfeld; Hans Schiessl, Pforzheim, both of Germany

[73] Assignee: Stratec Elektronik GmbH, Birkenfeld, Germany

[21] Appl. No.: 08/793,090

[22] PCT Filed: Aug. 11, 1995

[86] PCT No.: PCT/EP95/03188

§ 371 Date: Jun. 3, 1997

§ 102(e) Date: Jun. 3, 1997

[87] PCT Pub. No.: WO96/05514

PCT Pub. Date: Feb. 22, 1996

[30] Foreign Application Priority Data

Aug. 17, 1994 [DE] Germany ............... 44 29 155

[51] Int. Cl.⁶ ............... G01N 35/00; G01N 21/76; G01N 21/03; B03C 1/28
[52] U.S. Cl. ............... 436/49; 436/47; 436/48; 436/174; 436/177; 436/180; 422/63; 422/65; 422/101; 210/695; 210/222
[58] Field of Search ............... 422/63, 65, 67, 422/68.1, 81, 100, 101; 436/43, 47, 48, 49, 54, 174, 175, 177, 179, 180; 210/205, 222, 223, 695; 209/224, 232

[56] References Cited

U.S. PATENT DOCUMENTS

| | | | |
|---|---|---|---|
| 3,645,506 | 2/1972 | Selesnick | 259/58 |
| 5,147,529 | 9/1992 | Lee et al. | 210/695 |
| 5,599,501 | 2/1997 | Carey et al. | 422/64 |
| 5,705,062 | 1/1998 | Knobel | 210/205 |

*Primary Examiner*—Long V. Le
*Attorney, Agent, or Firm*—Antonelli, Terry, Stout & Kraus, LLP

[57] ABSTRACT

A measuring system and method are provided for performing luminometric series analyses on reaction components to be investigated and the liquid samples containing the magnetizable carrier particles binding said components. Sample chambers receive the liquid samples. These sample chambers are transported to a measuring station on a conveyor. Permanent magnets act on the sample chambers with magnetic fields during transport. A separating station is also provided, which is preferably equipped with a suction and rinsing device to remove the surplus reaction components separated from the carrier particles that accumulate on wall areas of the sample chambers under the influence of the magnetic fields.

31 Claims, 3 Drawing Sheets

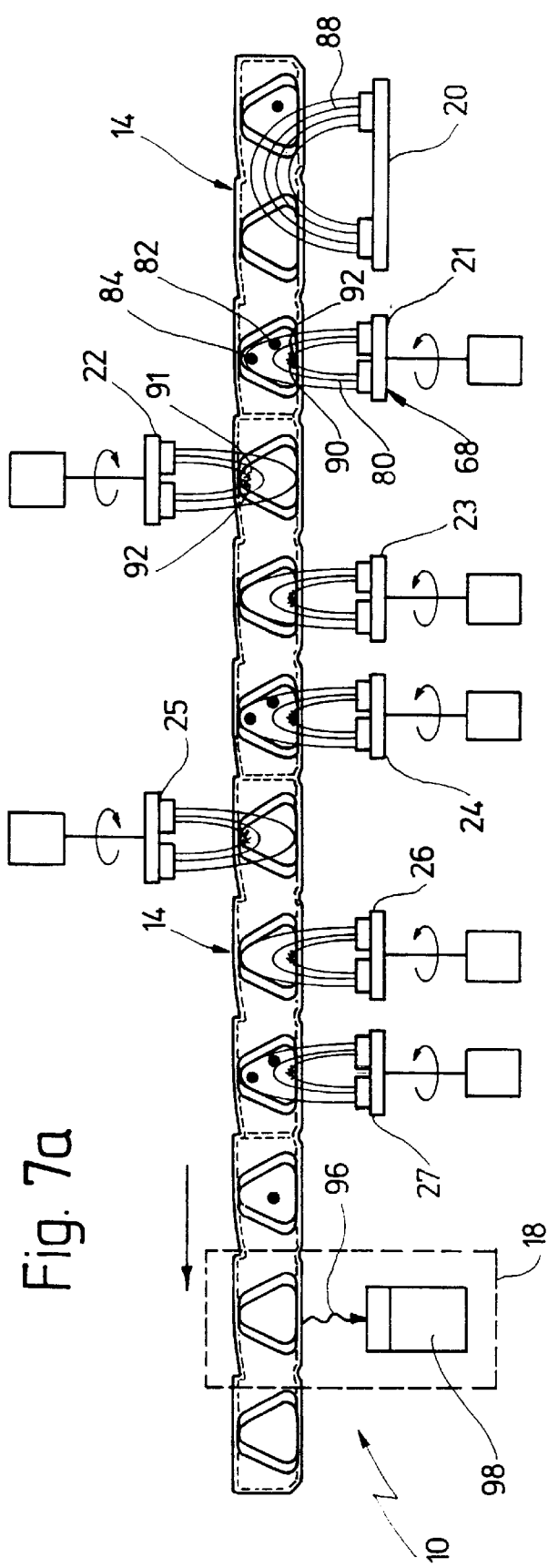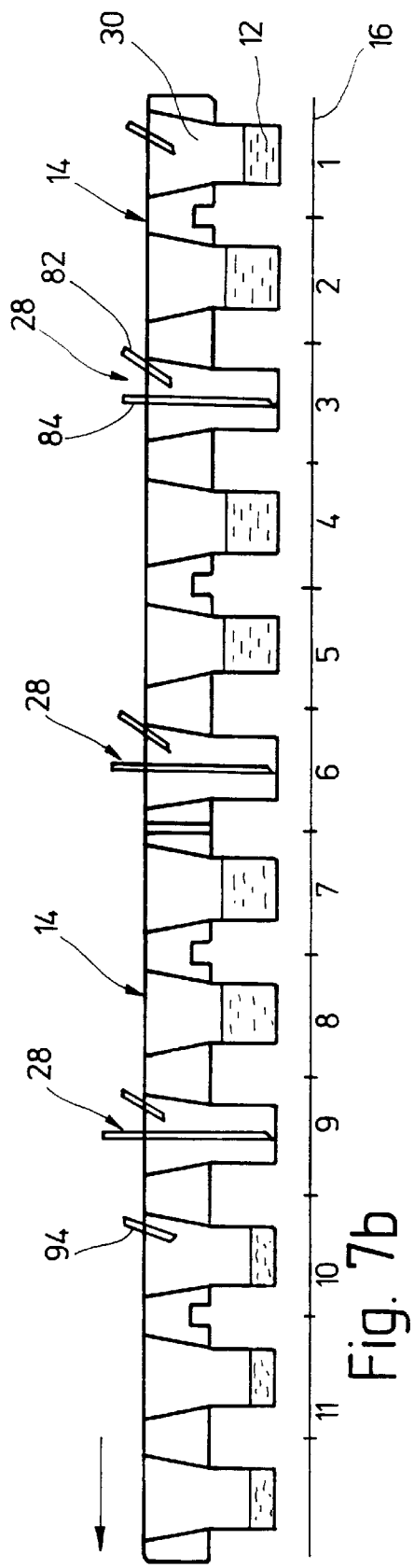

MEASURING SYSTEM AND METHOD FOR PERFORMING LUMINOMETRIC SERIES ANALYSES AS WELL AS MULTIPLE CUVETTE FOR RECEIVING LIQUID SAMPLES THEREFOR

Specification

The invention relates to a measuring system for performing luminometric series analyses on reaction components to be investigated and the liquid samples containing the magnetizable carrier particles binding said components, with a sample chamber that receives the liquid sample and can be transported to a measuring station on a conveyor, with a permanent magnet that acts on the sample chamber with its magnetic field during transport, as well as a separating station preferably equipped with a suction and rinsing device to remove the surplus reaction components separated from the carrier particles that accumulate on a wall area of the sample chamber under the influence of the magnetic field.

The invention also relates to a method for luminometric series analyses in which a sample chamber, filled with a liquid sample containing reaction components to be investigated and the carrier particles that are magnetizable and bind the latter, is transported on a conveyor to a luminescence measuring station with the carrier particles being accumulated during the course of transport in a collecting area of the sample chamber wall during a separating phase under the influence of a magnetic field and with surplus reaction components being removed from the sample chamber in a washing process that follows the separating phase.

Measuring techniques of this kind serve primarily in medical diagnosis, food-chemistry analysis, biotechnology, and environmental technology for specific and quantitative determination of very small amounts of biomolecules and toxins, with a large number of samples frequently having to be processed. For measurement, the target substances contained in a sample liquid are labeled in an immunochemical reaction with a specific antibody bearing a marker (luminogen) capable of luminescence. For concentration with chemical and physical agents, the target structure thus obtained is additionally coupled with a magnetic particle coated with specific antibodies and separated as quantitatively as possible from the liquid component under the influence of a magnetic field. This component can then be removed by suction or decanting. The measuring process itself takes place following the addition of a starting reagent that excites the luminogen and causes it to glow. The fluorescence photons then emitted are collected by a photodetector designed as a photomultiplier which "looks at" the sample volume in a darkened measuring station and produces a recording in the form of counting pulses. On the basis of the total photon yield determined in the form of integrated counting pulses, the concentration of the target substance is finally determined by a calibration relationship.

A device of the species recited at the outset is known (DE 39 26 462 A1) in which a large number of samples is fed in individual test tubes on a conveyor to a separating station. During transport, permanent magnets are introduced cyclically into the conveyor and carried along with the associated test tubes through a section of the conveyor. All of the permanent magnets in this conveyor section are aligned in the same way and cause the solid magnetic particles to accumulate at a specific point on the inside wall of each test tube. Although it is possible to use this device to permit the separating and washing procedures as well as the subsequent measurement process to take place fully automatically, the entire structure of this system is mechanically complex and requires a high operating cost due to the handling of a large number of individual tubes. In particular, however, it has been found that when the magnetic particles accumulate on the walls of the test tubes, they have a tendency to clump and to trap free luminogens because of their coating that bears the antibodies. During luminescence measurement, these luminogens then generate a certain amount of background noise from which the light signals from the target substances can no longer be distinguished below a resultant limiting concentration for detection.

Therefore the goal of the invention is to improve a measuring system and a method of the species recited at the outset as well as the associated multiple cuvette in such fashion that the measurement results are quickly available at a lower detection limit with reduced handling expense.

To achieve this goal, the combinations of features included in claims 1, 20, and 26 are proposed. Advantageous embodiments and improvements on the invention are contained in the dependent claims.

The solution according to the invention is based on the idea of connecting several sample chambers with one another as units that can be handled in common and adjusting these in conjunction with the magnetic field configuration in an optimum fashion to match the special nature of both the magnetic separating process and the optical measuring process. For this purpose, according to the invention it is proposed that a plurality of cuvette units each forming a sample chamber be connected together to form a multiple cuvette and that at least two permanent magnets be mounted along the conveyor with a distance between them, with the permanent magnets penetrating the cuvette units transported past them sequentially with their magnetic fields from wall areas that are opposite one another. The action of the magnets placed in stationary positions on both sides of the conveyor ensures in simple fashion that the magnetizable carrier particles that are attracted during cuvette transport will accumulate alternately, first on one side and then on the other, of the sample chambers, with the free luminogens that adhere to the carrier particles as they pass through the sample liquid redistributing themselves in the sample liquid.

According to one preferred embodiment of the invention, each permanent magnet is a double magnet that consists of two bar magnets that are preferably cylindrical, arranged parallel to one another with opposite polarity, with the double magnets being rotatable by means of a rotary drive around an axis of rotation that extends centrally and axially parallel, preferably horizontally, and transversely with respect to the conveyor. As a result, a magnetic field is generated that penetrates the cuvette units in the form of a lobe, under whose influence the carrier particles move along long spiral paths and can accumulate pointwise as pellets on the cuvette walls. The pellets can then be picked up in the peak area of the elliptical field line with sufficient attractive force by a double magnet located downstream with a mirror-symmetric action, without carrier particles settling in dead spaces in the individual cuvettes that are poor in field lines.

To generate a magnetic field that is as strong as possible, with a low distribution of the scattered field, the two bar magnets are preferably made of a metal alloy of the rare earths, and coupled magnetically by a yoke at their opposite poles that face away from the conveyor. A strong, highly bundled magnetic field permits rapid and efficient concentration of the magnetic particles and thus a high sample throughput.

In order to limit the action of the field primarily to the cuvette unit being carried past at any given moment, the two bar magnets of each double magnet are rigidly connected together at a distance that approximately corresponds to the cross section of the cuvette units.

A pulsed action of permanent magnetic fields on the individual cuvette units moving past can be achieved by mounting the double magnets along a section of the conveyor at intervals that correspond to those between adjacent cuvette units.

For preconcentration, at the beginning of this section of the conveyor, a nonrotatable double magnet is arranged horizontally, with bar magnets mounted approximately at intervals equal to those of adjacent cuvette units. With its extensive magnetic field, this double magnet penetrates the entire volume of the sample chamber, thus collecting carrier particles even from areas that could not be affected by double magnets downstream, with their more tightly bundled magnetic fields.

Advantageously, this separation process takes place in successive steps through at least one group of three double magnets arranged side by side, of which the last two in the transport direction are located on the same side of the conveyor and the first is located on the opposite side, with a separating station located at the position of the last double magnet. The first two double magnets serve for alternately attracting the carrier particles through the sample liquid, while the last double magnet further compresses the pellet that has already accumulated and keeps it away from the suction device of the separating station.

Another advantageous embodiment of the invention provides that the cuvette units have a lower measuring chamber area and a loading area that is located above and expands toward a loading opening. As a result, even with small measuring volumes, there is sufficient room for the engagement of a suction and rinsing device that can be lowered from above.

It is advantageous for the conditions of the optical measuring process for the cuvette units to be trapezoidal or triangular in cross section and to have a transparent optical measuring window that covers the entire measuring chamber area on one side wall. The large-area measuring window increases the outlet area for the luminescence radiation into the half-chamber on the detector side, while the sample chamber area that tapers toward the rear, in which the emitted radiation is in any event mainly reabsorbed in the cloudy suspension of carrier particles, still has sufficient cross-sectional area for the intervention of a suction device.

A dimensionally-stable multiple cuvette that can be manufactured economically has, in the form of a one-piece molded plastic part, preferably six cuvette units rigidly connected to one another by lateral, vertical connecting ribs running at the level of the loading areas and upper horizontal connecting surfaces at the level of the loading openings.

The handling of the multiple cuvettes during their introduction into the conveyor can be facilitated by insertion bevels located at their ends and formed by vertical cross members, each being aligned at an angle to the connecting surfaces and the connecting ribs on the measuring window side.

Advantageously, the multiple cuvette can be transported by means of a stepping system in a stepwise movement lengthwise along the conveyor. In this way it is possible to integrate the transport process in simple fashion into the measurement procedure that is characterized by a plurality of method steps that follow one another in time.

The interference of luminescence radiation between the cuvette units and the amount of light that passes between them can be reduced by a matte surface on the multiple cuvette that is roughened except for the measuring windows of the cuvette units. A further improvement in this regard can be achieved by the connecting ribs on the measuring window side and the opposite back of the multiple cuvette each being provided with an emission window. An additional benefit of the emission window as regards transport function is that the emission windows on the measuring window side are made in the form of transport stops that are recessed or project stepwise on the connecting ribs, said steps engaging a stepping pawl of the stepping system by a ramp, and that the emission window on the rear is designed as a latching bead for the engagement of a ball under pressure that secures the position of the multiple cuvette in the stepping system.

To prevent rotation, the multiple cuvette advantageously has centering recesses for the engagement of a centering fork, said recesses advantageously being located eccentrically, formed on the connecting ribs, and open at the bottom.

In order to add residual liquid during the suction action of a suction needle of the suction device that can be lowered into the cuvette, the cuvette units can have bottoms that slope downward from their measuring window sides to the opposite rear sides.

In accordance with the method, the abovementioned goal of the invention is achieved by virtue of the fact that the carrier particles, during the separating phase and under the influence of at least two magnetic fields that pass through the sample chamber sequentially and pass through opposite wall areas, are pulled between two spatially separate collecting areas through the liquid sample.

Preferably the carrier particles are pulled on spiral paths through the liquid sample under the influence of two rotating magnetic fields produced by two permanent bar magnets with opposite polarity that rotate around a common central axis, and accumulate in the collecting areas as pellets. Along the long spiral paths, an effective separation of the previously accumulated carrier particles takes place together with increased separation from free surplus luminogens that are not bonded to the target substance.

The latter can thus be removed from the sample by virtue of the fact that the washing process, in the case of magnetic particles that accumulate in the form of pellets on the sample chamber wall, is performed under the continued action of the rotating magnetic field by injecting and sucking away a rinse fluid. To further increase detection sensitivity and to suppress the noise caused by free luminogens, a plurality of successive separating phases and washing processes can be provided in the course of the transport of the sample chambers.

A continuous automatable sample throughput can be made possible by virtue of the fact that a plurality of sample chambers is transported simultaneously on the conveyor in the form of the cuvette units of a multiple cuvette that are connected together and are preferably made trilateral and prismatic. The multiple cuvettes can then be introduced in succession into the conveyor and can be transported as a connected train of cuvettes lengthwise on the conveyor in a stepped motion.

The invention will now be described in greater detail with reference to an embodiment shown schematically in the drawing.

Figure 1:
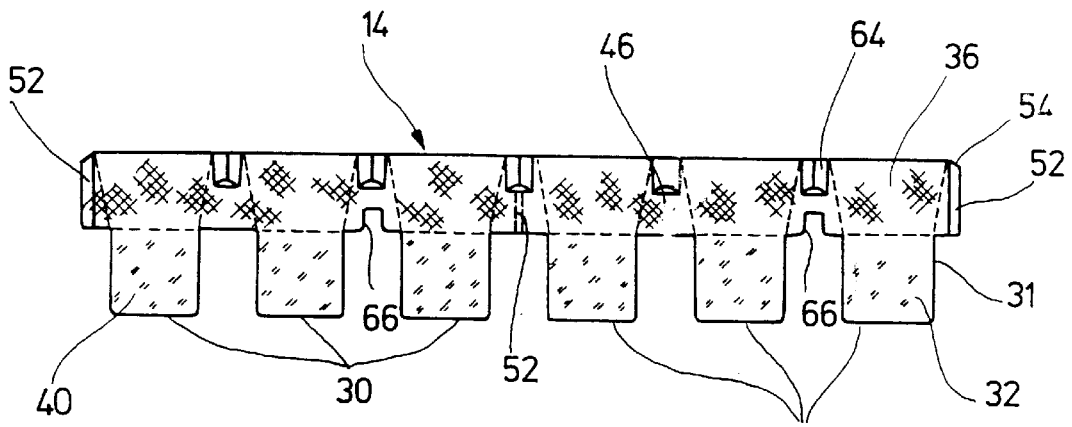
FIGS. 1 to 3 show a multiple cuvette with six cuvette units in a front view, top view, and rear view.
Figure 2:
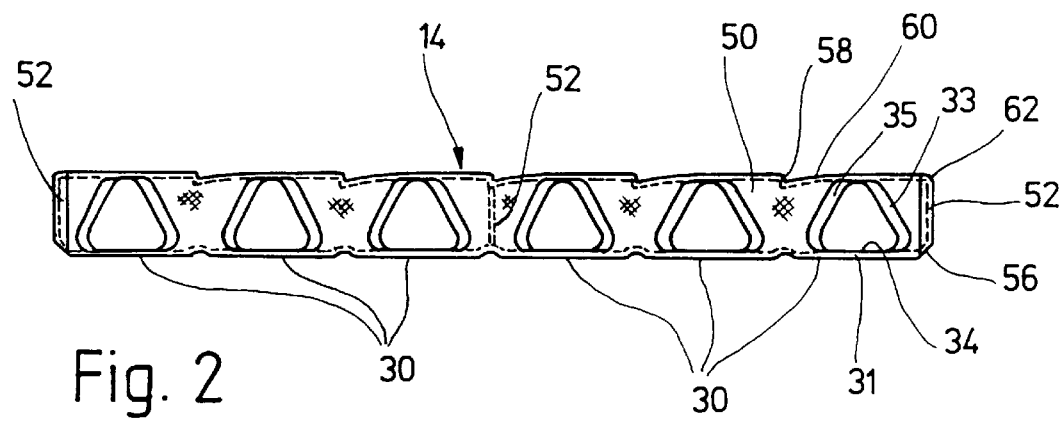
Figure 3:
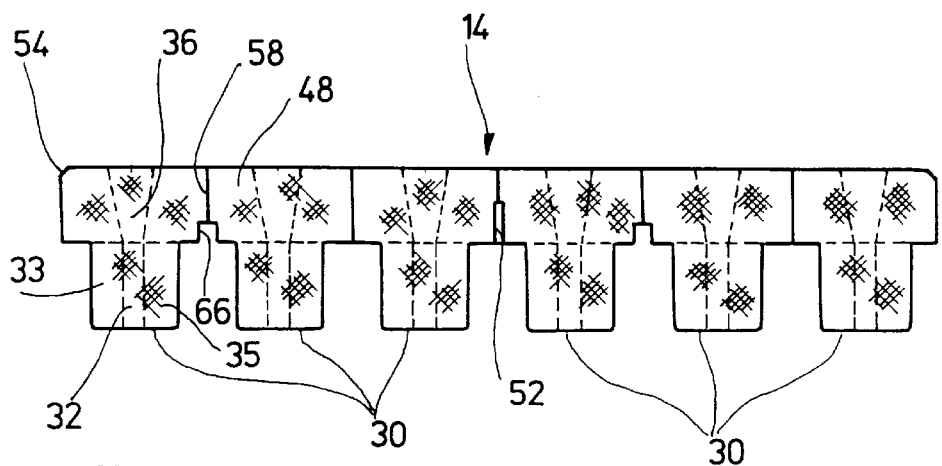
Figure 4:
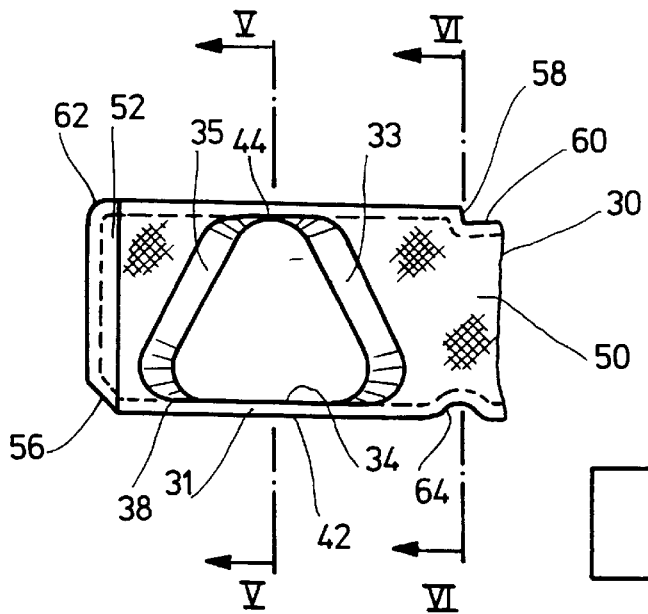
FIG. 4 is a representation, enlarged in sections, of a cuvette unit of the multiple cuvette in the top view in FIG. 2.
Figure 8:
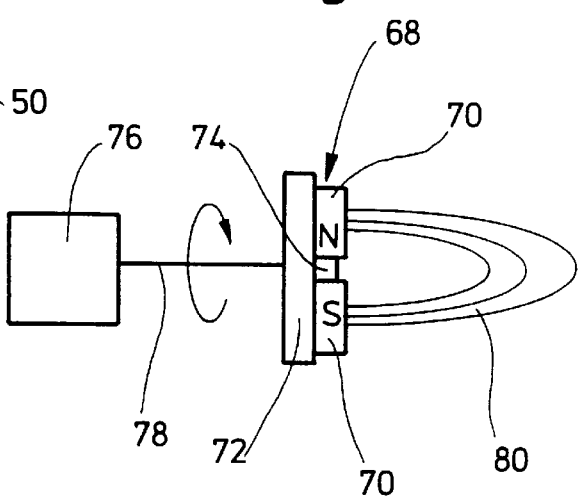
Figure 5:
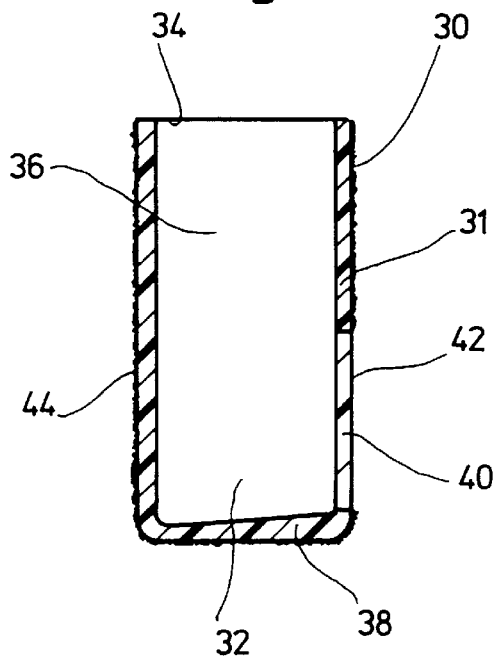
FIG. 5 is a section through the sample chambers of the individual cuvettes along line V—V in FIG. 4.
Figure 6:
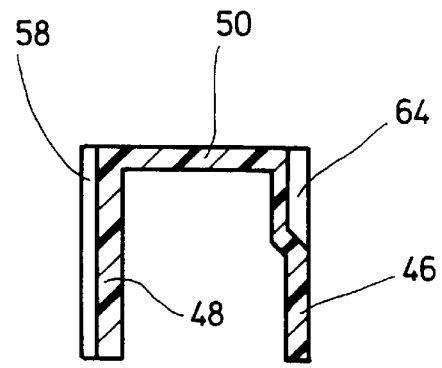
FIG. 6 is a section along line VI—VI in FIG. 4.

FIG. 7a is a measuring system for performing luminometric series analyses as seen in a top view; and FIG. 7b shows the measuring system according to FIG. 8a in a view from the measuring window side of the cuvette units in their respective transport positions on the conveyor; and FIG. 8 is an enlarged view of a double magnet used in the measuring system according to FIG. 7a and made in the form of a horseshoe magnet.

The measuring system 10 shown in FIGS. 7a and b serves to perform luminometric series analyses on liquid samples containing target substances to be detected and the labeling substances connectable with them in an immunochemical detection reaction as well as magnetizable carrier particles. Liquid samples 12 are transported in a multiple cuvette 14 along a conveyor 16 to a measuring station 18, with permanent magnets 20–27 designed as double magnets 68 and separating stations 28 intended to separate surplus labeling substance acting on multiple cuvettes 14 during transport.

The multiple cuvette 14 shown in FIGS. 1 to 6 is formed as a one-piece molding from a plastic that is permeable to light and has six connected cuvette units 30 joined in a row with equal spaces between them. The cuvette units 30 designed as trilateral prismatic hollow bodies, have a lower measuring chamber area 32 and a loading area 36 above that expands at the top to form a loading opening 34. One side wall 31 of cuvette units 30 that are triangular in cross section is designed in measuring chamber area 32 as a surface-polished transparent measuring window 40 that extends to cuvette bottom 38, while the other side walls 33, 35 have a surface that is rough and matte on the outside. At their connecting points, side walls 31, 33, 35 are connected together by internally concave wall areas. Cuvette bottom 38 is inclined downward from measuring window side 42 to the opposite rear side 44. The rigid connection of cuvette units 30 to form a multiple cuvette 14 is achieved by connecting ribs 46, 48 on the measuring window side and on the rear that run at the level of loading areas 36 and by upper connecting areas 50 that run at the level of loading openings 34, with multiple cuvette 14 being made more rigid by cross members 52 arranged at the ends and center. In addition, connecting ribs 46, 48, connecting areas 50, and cross members 52 have a roughened surface structure.

For introduction into conveyor 16, multiple cuvette 14 is provided on its ends with insertion bevels 54, 56 arranged at an angle to connecting areas 50 and connecting ribs 46 on the measuring window side. In order to permit transport in conveyor 16 by means of a stepping system, not shown, multiple cuvette 14 has on its rear connecting ribs 48 transport stops 58 that project inward stepwise, said stops engaging a stepping pawl of the stepping system by a ramp 60. Hence, the edge 62 that is at the rear and is not beveled also serves as a transport stop. In addition, latching beads 64 are provided on connecting ribs 46 on the measuring window side opposite transport stops 58 for the engagement of a ball under pressure that secures the position of multiple cuvette 34 in the stepping system. To prevent rotation when multiple cuvette 14 is inserted into conveyor 16, centering recesses 66 located opposite one another and open at the bottom are provided in connecting ribs 46, 48 at two positions that are asymmetric with respect to the arrangement of cuvette units 30, for the engagement of a centering fork.

As shown in FIG. 8, each double magnet 68 consists of two cylindrical bar magnets 70 with opposite polarity mounted parallel to one another, said magnets being coupled by a yoke 72 to form an arrangement in the shape of a horseshoe magnet. The two bar magnets 70 are kept apart from one another by a separating layer 74 made of plastic at a distance that is approximately equal to the width of the measuring windows of cuvette units 30. Double magnets 68 formed in this manner are rotatable by means of a rotary drive 76 around a rotational axis 78 that is centrally axially parallel to bar magnets 70, thus producing a rotating magnetic field 80 that extends in the shape of a lobe into the half space located in front of their free poles.

According to FIG. 7 the individual rotatable double magnets 21–27 are located at stationary positions 3–9 with the spacing of adjacent cuvette units 30 in multiple cuvette 14 along conveyor 16 on both sides of the latter, with rotational axes that are aligned transversely with respect to conveyor 16. At the beginning of conveyor 16 (positions 1 and 2) a nonrotatable double magnet 20 is mounted horizontally whose bar magnets are mounted approximately at the spacing of two adjacent cuvette units 30.

Along conveyor 16, a plurality of separating stations 28 equipped with suction and rinsing devices is mounted above multiple cuvettes 14 being transported, said devices being lowerable under program control in such fashion that they submerge an injection needle 82 for rinsing fluid into loading area 36 of a cuvette unit 30 located beneath and a suction needle 84 into the rear area of cuvette unit 30 down to bottom 38 of the cuvette.

To perform a measurement, the liquid material 12 to be investigated along with the target substances to be determined therein, together with a surplus of an antibody against the target substance as well as a marker substance containing luminogens, is added to cuvette units 30. At the same time, carrier particles that are magnetizable and made of iron are suspended in material 12 to be investigated, said particles having a grain size of about 10 $\mu$m and having their exteriors coated with a latex layer that also contains specific antibodies against the target substance.

The antibodies of the carrier particles and the labeling substance "recognize" the target molecules to be detected and bind them in an immunochemical reaction. As a result, specific complexes of carrier particles and molecules of the target and labeling substances are formed. In an incubation process lasting on the order of several minutes to hours, the reaction is brought to equilibrium for the most part at constant temperature. The actual determination is performed optically, with the luminogens being excited to glow at measuring station 18 and the yield of luminescence radiation thus produced being measured. In order not to distort the measurement results, the free luminogens that are not bonded to target molecules must be removed from the sample prior to luminescence measurement. For this purpose the substance 12 to be investigated is subjected in the manner described below to a separating process that takes place during transport to measuring station 18, said method being performed stepwise corresponding to a stepwise transport movement of cuvette units 30.

Initially the multiple cuvettes 14 loaded with the samples are introduced by an automatic handling unit, not shown, of measuring system 10 into conveyor 16. Then the cuvette unit 30 which at that moment is located at input position 1 of conveyor 16 receives additional liquid buffer (injection needle 86) and the substance to be investigated is exposed for the duration of two transport steps to the extensive magnetic field of the first static double magnet 20. Under the influence of magnetic field 88 the iron particles in measuring chamber area 32 are preconcentrated in measuring chamber area 32 on the inside of the measuring window side. At the next position (position 3), a rotating double magnet 21 that acts transversely from the same side of conveyor 16 compresses the accumulated magnetic particles into a pellet 92 in the form of a dot. Compression is performed by rotating magnetic field 80 in such fashion that the iron particles are moved on spiral paths into the area of higher field strengths and, at the center of ellipsoid magnetic field 80, accumulate on the interior of measuring window 40 in a collecting area 90. Then magnetic field 80 of double magnet 68, which in terms of its configuration approximately conforms to the inside contour of cuvette unit 30, extends with sufficient attractive force to the opposite rear side 44. The concave wall connections of side walls 31, 33, and 35 of the individual cuvettes 30 also prevent carrier particles from settling in corner areas that would otherwise not be reachable by magnetic field 80. Following this separation, the removal by suction of the remaining material to be investigated takes place at the same position 3. For this purpose, suction needle 84 is used which can be inserted into rear measuring chamber area 32 while maintaining a sufficiently large distance from pellet 92, with pellet 92 adhering to the side wall because magnetic field 80 is maintained. The nonbonded luminogen is largely removed along with the fluid that is drawn off. Then rinse fluid is added again by means of injection needle 82. At the next transport position 40, the pellet is picked up in the peak area of the magnetic field of the next double magnet 22 that penetrates from the back 44 of cuvette unit 30 and is vorticized spiral-fashion in the rinsing liquid so that the free luminogens still contained therein are dissolved again. Following the formation of a pellet 92, in the next two transport steps 5 and 6, under the influence of double magnets 23, 24 that act from measuring window side 42 at the corresponding positions, a renewed vorticization and accumulation of the carrier particles at measuring window 40 takes place, followed by another suction and injection process. The same method steps are repeated a final time at the next transport positions 7, 8, 9 under the successive influence of another group of three double magnets 25, 26, 27 and completed by a resuspension (injection needle 94) of the carrier particles at position 10. Then cuvette unit 30 is moved to darkened measuring station 18 where a luminescence reaction of the luminogens is activated by adding additional reagents. The luminescence radiation 96 that passes through measuring window 40 and declines in the course of a few seconds is detected by photodetector 98 and evaluated integrally taking into account calibration relationships and calibration measurements regarding the concentration of target substance.

In summary, therefore, the following can be determined: the invention relates to a measuring system and a method for performing luminometric series analyses on reaction components to be investigated and on the liquid samples 12 containing magnetizable carrier particles binding said components. The samples are transported in cuvette units 30 of a multiple cuvette 14 on a conveyor 16 to a measuring station 18 where the concentration of the target substance to be determined is determined by a luminescence measurement. To remove surplus reaction components that would distort measurement, multiple cuvettes 14 are transported past a plurality of rotating permanent magnets 20–27, said magnets, with their lobe-shaped magnetic fields 80, penetrating cuvette units 30 sequentially and from opposite wall areas 40, 44. As a result the carrier particles are carried along spiral paths through the sample liquid and concentrated as pellets 92. The surplus reaction components separated from the carrier particles can then be removed in a rinsing and suction process.

I claim:

1. A measuring system for performing luminometric series analyses on liquid samples containing reaction components to be investigated and on magnetizable carrier particles binding the reaction components, with sample chambers that contain the liquid samples, a conveyor for transport of the sample chambers to a measuring station, a permanent magnet that acts during transport with its magnetic field on the sample chambers and a separating station for removing the surplus reaction components separated from the carrier particles that are accumulated under the influence of the magnetic field on wall areas of the sample chambers, characterized by a multiple cuvette that consists of cuvette units connected together in a row and each forming one of the sample chambers, and at leas two permanent magnets located at intervals along the conveyor, said magnets penetrating cuvette units transported past them sequentially and alternately from wall areas opposite one another with their magnetic fields wherein each permanent magnet is a double magnet comprised of two bar magnets mounted parallel to one another with opposite polarity and positioned on the same side of the sample chambers.

2. A measuring system according to claim 1, characterized in that said double magnets are rotatable by means of a rotary drive around a rotational axis that is centrally axially parallel with respect to said bar magnets that is centrally axially parallel with respect to said bar magnets, that is substantially horizontal, and that extends transversely to the conveyor.

3. A measuring system according to claim 2, characterized in that the two bar magnets of each double magnet which are comprised of a metal alloy of the rare earths are coupled magnetically at their unlike poles facing away from the conveyor by a yoke.

4. A measuring system according to claim 2 or 3, characterized in that the two bar magnets of each double magnet (68) are rigidly connected together by a separating layer comprised of plastic, with a distance between them that approximately corresponds to the cross sections of cuvette units (30).

5. A measuring system according to one of claims 2 or 3, characterized in that the double magnets are arranged at the spacing of adjacent cuvette units of multiple cuvettes along the conveyor.

6. Measuring system according to one of claims 2 or 3, characterized in that a nonrotatable double magnet (20) is located horizontally at the beginning of conveyor (16), the bar magnets of said magnet being mounted approximately at the spacing of two adjacent cuvette units (30).

7. A measuring system according to one of claims 2 or 3, characterized by at least one group of three double magnets being located next to one another along the conveyor, of which the last two in the transport direction are located on the same side and the first is located on the opposite side of the conveyor, and by a separating station located at a position of the last double magnet.

8. A measuring system according to one of claims 1 or 3, characterized in that the cuvette units have a lower measuring chamber area and a loading area located above and expanding upward to form a loading opening.

9. A measuring system according to one of claims 1 or 3, characterized in that the cuvette units are made trapezoidal or triangular in cross section and have a transparent optical measuring window that covers a measuring chamber area on one side wall.

10. A measuring system according to claim 8, characterized in that a multiple cuvette formed as a one-piece molded part from plastic, has 4 to 8 cuvette units that are rigidly connected together by lateral vertical connecting ribs that run at the level of loading area and by horizontal connecting areas that are located at the level of loading openings.

11. A measuring system according to claim 10, characterized in that the multiple cuvette has insertion bevels for insertion into the conveyor at its ends formed by vertical cross members, said bevels running diagonally with respect to connecting areas and connecting ribs on a measuring window side.

12. A measuring system according to claims 10, characterized in that the multiple cuvette is transportable lengthwise by means of a stepping system in a stepwise motion in the conveyor.

13. A measuring system according to claims 10, characterized in that the multiple cuvette has a roughened matte surface, except for measuring windows of the cuvette units.

14. A measuring system according to claim 11, characterized in that the connecting ribs on the measuring window side and an opposite rear side of the multiple cuvette each have emission windows that prevent light from passing between adjacent cuvette units.

15. A measuring system according to claim 14, characterized in that the rear emission windows are also formed as transport stops that are recessed or project stepwise at the connecting ribs, said stops meshing by a ramp (60) with a stepping pawl of the stepping system.

16. A measuring system according to claim 14, characterized in that the emission windows on the measuring window side are simultaneously designed as latching beads for the engagement of a ball under pressure that secures the position of the multiple cuvette in the stepping system.

17. A measuring system according to claim 10, characterized in that the multiple cuvette has centering recesses for the engagement of a centering fork, said recesses being located eccentrically on the multiple cuvette and formed on the connecting ribs, as well as being open toward the bottom.

18. A measuring system according to one of claims 1 or 3, characterized in that the cuvette units have a floor that slopes downward from measuring window sides to the opposite rear sides.

19. A measuring system according to claim 8, characterized in that the separating station has an injection needle, insertable into the loading area, for rinsing fluid and a suction needle that can be submerged in the rear area of the cuvette unit down to the cuvette bottom.

20. A method for luminometric series analyses in which sample chambers filled with a liquid sample, containing reaction components to be investigated and magnetizable carrier particles binding the latter, are transported in a conveyor to a luminescence measuring station, with the carrier particles being accumulated during transport under the action of a magnetic field during a separating phase in collecting areas of sample chamber walls and with excess reaction components being removed from the sample chambers in a rinsing process that follows the separating phase, characterized in that the carrier particles, under the influence of at least two magnetic fields that penetrate the sample chambers sequentially in time and alternately from opposite wall areas are drawn through the liquid sample during the separating phase between two collecting areas separated in space, wherein each of the magnetic fields is respectively provided by one of a permanent magnets, wherein each of the permanent magnets is a double magnet comprised of two bar magnets mounted parallel to one another, with opposite polarity and positioned on the same side of the sample chambers.

21. A Method according to claim 20, characterized in that the carrier particles are drawn along spiral paths through liquid sample under the influence of rotating magnetic fields and are accumulated in collecting areas as pellets.

22. A Method according to claim 20 or 21, characterized in that the rinsing process is performed with the magnetic particles accumulated as pellets on sample chamber wall by injecting and drawing off a rinsing fluid under suction while maintaining rotating magnetic field.

23. A Method according to one of claims 20 or 21, characterized in that a plurality of successive separating phases and rinsing processes are performed in the course of the transport of sample chambers (30).

24. A Method according to one of claims 20 or 21, characterized in that a plurality of sample chambers are transported simultaneously in the conveyor in the form of cuvette units that are connected together in series and are preferably shaped to be trilateral or prismatic.

25. A Method according to claim 24, characterized in that a plurality of multiple cuvettes are introduced sequentially into the conveyor and are transported as a connected train of cuvettes lengthwise and stepwise in the conveyor.

26. A measuring system according to claim 4, characterized in that the double magnets are arranged at the spacing of adjacent cuvette units of multiple cuvettes along the conveyor.

27. A measuring system according to claim 4, characterized in that a nonrotatable double magnet is located horizontally at the beginning or the conveyor, the bar magnets of said magnet being mounted approximately at the spacing of two adjacent cuvette units.

28. A measuring system according to claim 4, characterized by at least one group of three double magnets being located next to one another along the conveyor, of which the last two in the transport direction are located on the same side and the first is located on the opposite side of the conveyor, and by a separating station located at a position of the last double magnet.

29. A measuring system according to claim 4, characterized in that the cuvette units have a lower measuring chamber area and a loading area located above and expanding upward to form a loading opening.

30. A measuring system according to claim 4, characterized in that the cuvette units are made trapezoidal or triangular in cross section and have a transparent optical measuring window that covers a measuring chamber area on one side wall.

31. A measuring system according to claim 4, characterized in that the cuvette units have a floor that slopes downward from measuring window sides to the opposite rear sides.

* * * * *